United States Patent [19]

Hognat et al.

[11] 4,145,912
[45] Mar. 27, 1979

[54] METHOD AND APPARATUS FOR MEASURING VISCO-ELASTICITY OF COMPOSITE SHEET MATERIAL

[75] Inventors: Jacques L. P. Hognat, Rueil Malmaison; Jean-Louis Van Den Berghe, Pontoise, both of France

[73] Assignee: Societe Nationale Industrielle Aerospatiale, Paris, France

[21] Appl. No.: 855,840

[22] Filed: Nov. 30, 1977

[30] Foreign Application Priority Data

Dec. 6, 1976 [FR] France .................................. 76 36663

[51] Int. Cl.² ............................................. G01N 3/32
[52] U.S. Cl. ......................................... 73/15.6; 73/159
[58] Field of Search ................................. 73/15.6, 159

[56] References Cited

U.S. PATENT DOCUMENTS

| | | | |
|---|---|---|---|
| 3,039,297 | 6/1962 | Peter et al. | 73/15.6 X |
| 3,531,996 | 10/1970 | Harris et al. | 73/15.6 X |
| 4,034,602 | 7/1977 | Woo | 73/15.6 X |

Primary Examiner—Herbert Goldstein
Attorney, Agent, or Firm—Merriam, Marshall & Bicknell

[57] ABSTRACT

The present invention relates to a method and apparatus for measuring the viscoelasticity of a sheet material comprising a flexible organic and/or inorganic reinforcement impregnated with a synthetic resin, wherein a sample of said sheet is subjected to a heating cycle and, during this cycle, said sample is held stretched between two of its spaced-apart zones and a maintained reciprocating movement of constant amplitude, of direction coplanar with respect to the plane of said sample and transverse with respect to the direction of tension thereof, is imparted to one of said zones, then the variations in amplitude of the reciprocating movement transmitted to the other of said zones with the rise in temperature are observed. The invention is more particularly applied to the manufacture of composite pieces by assembling, by hot-pressing, a plurality of sheets impregnated with resin.

10 Claims, 5 Drawing Figures

METHOD AND APPARATUS FOR MEASURING VISCO-ELASTICITY OF COMPOSITE SHEET MATERIAL

The present invention relates to a method and apparatus for the dynamic study, as a function of the temperature, of the visco-elasticity of a composite sheet material comprising a flexible organic and/or inorganic reinforcement impregnated with synthetic resin.

It is known that, for producing certain shaped pieces, a stack of sheets of a composite material comprising a flexible reinforcement impregnated with synthetic resin is disposed in a suitable mould. The reinforcements of these sheets may for example be constituted by glass fibres, carbon fibres or fibres known commercially under the name of KEVLAR. The stack of sheets is subjected in said mould to a rise in temperature and to a pressure tending to apply the different sheets of the stack against one another. The purpose of the rise in temperature is firstly to soften the resin, then, after application of the pressure, to polymerise this resin. In this way, due to the choice of the temperature cycle to which the stack of sheets in subjected and of the pressure applied thereon, it is possible to join said sheets together.

To ensure satisfactory joining of the sheets, it is indispensable on the one hand that the application of the pressure on the stack of impregnated sheets occurs at a precise instant of the heating cycle of the resin at which said resin has the optimum viscosity and, on the other hand, that the pressure has a correct value.

In fact, if the pressure is applied at a moment when the resin is too liquid, or if the pressure is too high, a large quantity of the resin is driven out of the reinforcements and a shaped piece is obtained which comprises too high a proportion of reinforcement with respect to the resin and the mechanical interlaminar shear characteristics are weak. On the other hand, if the pressure is applied during the heating cycle at a moment when the resin is in a semi-solid state, or if the pressure is not strong enough, a shaped piece is obtained which comprises too much resin with respect to the reinforcements and the adhesion between the different sheets is weak.

At present, the application of pressure on the stack of impregnated sheets during the heating cycle is most often effected by trial and error, without the viscoelastic state of the resin nor the adequate value of the pressure to be applied being exactly known.

It may be noted that apparatus for measuring the viscoelastic parameters of the resins in torsion and in flexion are already known. However, the measurements are not carried out dynamically, an impulse being given to the material after which the logarithmic decrement of this impulse is measured at a given instant or at a given temperature, this meaning that such apparatus cannot be easily used for the application mentioned hereinabove.

It is an object of the present invention to remedy these drawbacks. It relates to a method and apparatus enabling the optimum temperature and pressure to be applied to the stack of flexible, impregnated sheets to be determined, in order to obtain a composite assembling of impregnated sheets having high mechanical characteristics. The invention enables a directly exploitable measurement to be furnished without the necessity of a programme for processing the results.

To this end, according to the invention, the method for measuring the visco-elasticity of a sheet material comprising a flexible reinforcement impregnated with a synthetic resin, is noteworthy in that a sample of said sheet is subjected to a heating cycle and in that, during the cycle, said sample is held stretched between two of its spaced-apart zones and a maintained reciprocating movement of constant amplitude, of direction coplanar with respect to the direction of the tension thereof, is imparted to one of said zones, then the variations in amplitude of the reciprocating movement transmitted to the other of said zones are observed.

Thus, due to the invention, the state of viscosity of the synthetic resin impregnating the same can be determined by observing the development of the amplitude of the reciprocating movement transmitted.

The method and apparatus of the invention are particularly useful in connection with the manufacture of articles formed by hot-pressing a plurality of superposed resin-impregnated sheets. In such application of the invention, a stack of additional samples of sheet material identical to that under test is simultaneously subjected to the same heating cycle. When the indicated viscoelasticity of the single sample shows that an appropriate pressing temperature has been reached, the stack is compressed under a controlled mechanical pressure. By carrying out this procedure at different temperatures and with different applied pressures and examining the mechanical properties of the compressed stack, the optimum combinations of temperature and pressure to be used in assembling articles from the sheets of material can be determined.

The variations in amplitude of the reciprocating movement transmitted by the first sample may be directly observed. However, it is sometimes preferable if these variations are compared with the constant amplitude of the maintained reciprocating movement. The result of the comparison is then observed.

In order to carry out the method of the invention, an apparatus according to the invention advantageously comprises means for subjecting said sample to a heating cycle, spaced-apart gripping means for gripping said sample and holding it stretched, means for animating one of said gripping means with a maintained reciprocating movement of direction coplanar with respect to said sample and transverse with respect to the tension thereof and means for detecting the variations in amplitude of the reciprocating movement transmitted to the other of said gripping means, through the sample. In an advantageous embodiment, the device according to the invention comprises, on the one hand a heating chamber inside which are arranged two spaced apart, coplanar pairs of jaws, adapted to be displaced parallel to each other in their common plane and, on the other hand, a reciprocating movement generator mechanically connected to one of said pairs of jaws and a displacement pick-up connected to the other pair of jaws.

The reciprocating movement generator may comprise a motor and a crank-connecting rod system, said connecting rod being pivoted at its free end on the corresponding pair of jaws and being disposed substantially in the common plane of said pair of jaws, whilst the connection between the displacement pick-up and the other pair of jaws is effected by a displacement pick-up rod parallel to said connecting rod.

The reciprocating movement generator and the displacement pick-up may be disposed outside the heating chamber and the connecting rod and displacement pick-up rod may pass through a wall thereof through tight passages.

Each pair of jaws is preferably disposed at the end of at least one spring leaf, the other end of which is fast with the chamber and the plane of which is at right-angles to the direction of displacement of the jaws.

Moreover, in order to determine the optimum pressure to be applied on the stack of sheets, in the manner indicated hereinabove, the apparatus according to the invention advantageously comprises a plurality of presses disposed inside the chamber and each associated with an additional sample similar to the sample subjected to the reciprocating movement.

The invention will be more readily understood on reading the following description with reference to the accompanying drawings in which.

Figure 1:
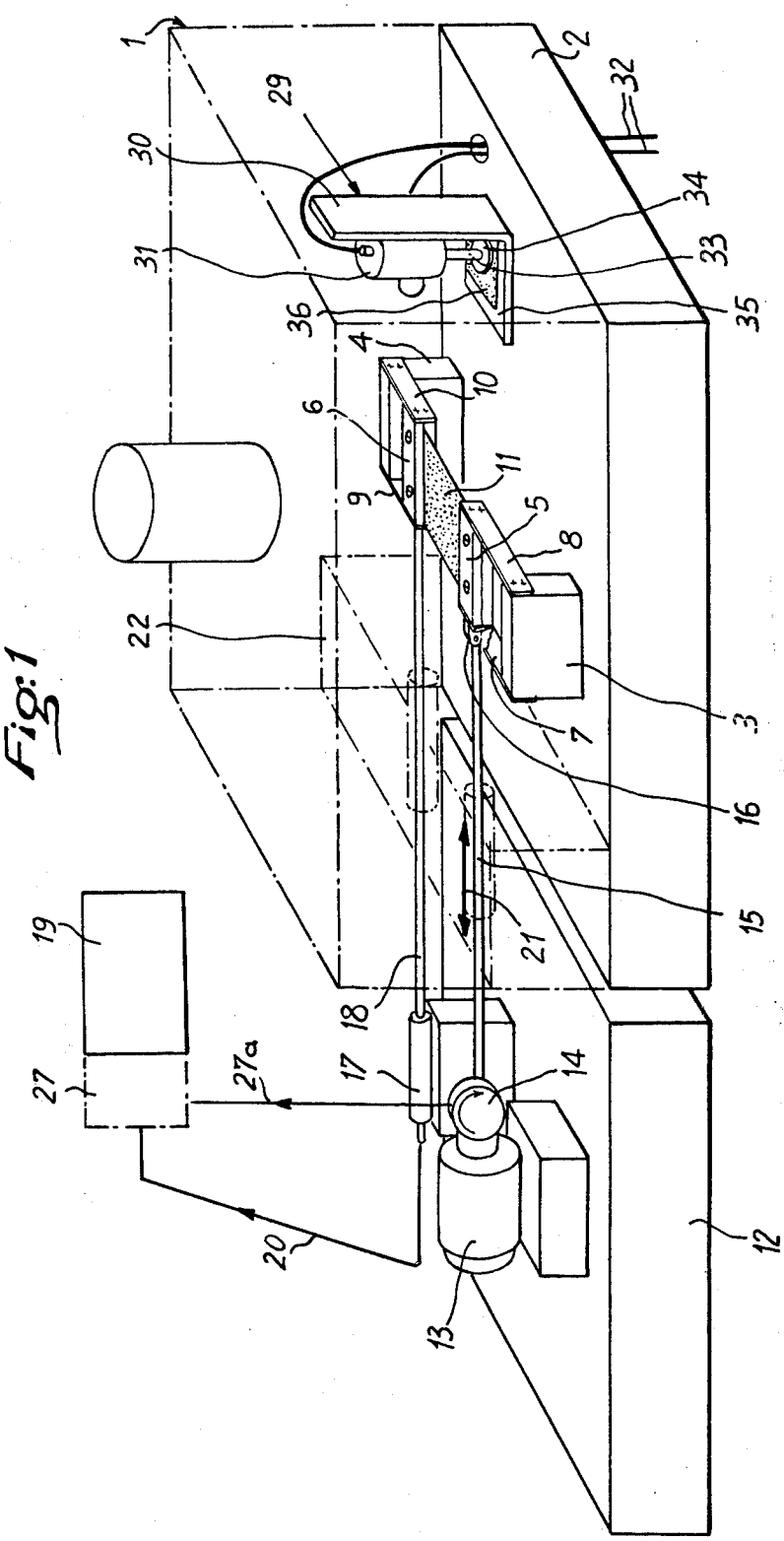
FIG. 1 is a schematic view in perspective of an embodiment of an apparatus for carrying out the method according to the invention.

Referring now to the drawings, FIG. 1 shows the apparatus according to the invention which comprises a ventilated heating chamber 1, the upper part of which has been shown in broken lines so as to show the members that it contains.

On the base 2 of the chamber 1 are disposed two opposite fixed supports 3 and 4, each bearing a pair of jaws 5 or 6. The pairs of jaws 5 is connected to the fixed support 3 via lateral spring leaves 7 and 8 disposed parallel to each other and enabling the pair of jaws 5 to move in a horizontal plane.

Similarly, the pair of jaws 6 is connected to the fixed support 4 via two spring leaves 9 and 10 enabling said pair of jaws 6 to move in the same horizontal plane as the pair of jaws 5. The planes of the spring leaves 7 to 10 are vertical so that the pairs of jaws 5 and 6 cannot move in a vertical plane.

Between the pairs of jaws 5 and 6, a sample 11 of a composite sheet comprising a flexible organic and/or inorganic reinforcement impregnated with synthetic resin is held stretched.

Outside the chamber 1 is disposed a support 12 on which is mounted an electric motor 13. The output shaft of the motor 13 is connected to the pair of jaws 5 via a cam device 14 and a connecting rod 15, of which the end opposite the cam device 14 is pivoted at 16 on said pair of jaws 5.

Furthermore, the support 12 bears a displacement pick-up 17 connected to the pair of jaws 6 by a displacement pick-up rod 18 of fixed length. This pick-up 17 is of known type enabling the longitudinal reciprocating movements of the rod 18 to be converted into an electric signal transmitted to a recorder 19 via an electric line 20.

The connecting rod 15 and rod 18 are substantially horizontal and parallel to each other and they pass through the wall of the chamber 1 via a tight guiding device 22.

The apparatus of FIG. 1 functions as follows:

The sample 11 is subjected, via the chamber 1, which is controlled by a device which has not been shown in the drawings, to a rise in temperature. The law of development of the temperature as a function of time may be chosen as desired. For simplification purposes, it has been assumed, in the example of FIG. 5, that the temperature T varied linearly with time t.

Figure 2:
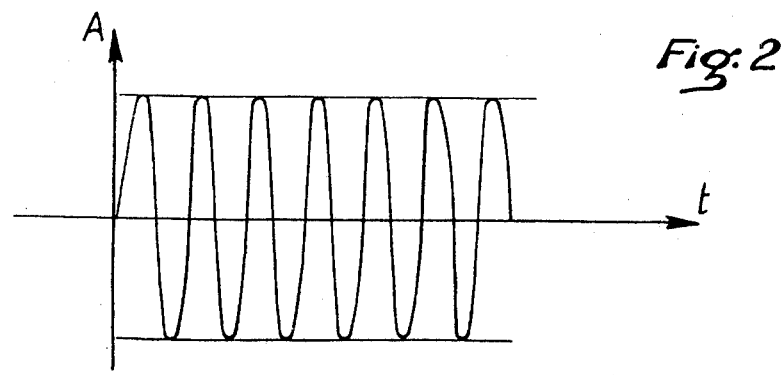
FIG. 2 is a graph showing the reciprocating movement of constant amplitude applied to one end of a sample of sheet material under test, during the heating cycle.

The motor 13 is actuated whilst the sample 11 is subjected to this rise in temperature. Consequently, due to the cam device 14 and to the connecting rod 15, the pair of jaws 5 is subjected to a reciprocating movement in the longitudinal axis of the connecting rod 15. This reciprocating movement is indicated by the double arrow 21. FIG. 2 illustrates the reciprocating movement of the pair of jaws 5, of which movement the amplitude A is constant.

Due to the presence of the sample 11 stretched between the pairs of jaws 5 and 6, the longitudinal reciprocating movement of the pair of jaws 5 is transmitted to the pair of jaws 6 which is therefore also animated by a reciprocating movement in the longitudinal axis of the rod 18.

As long as the temperature inside the chamber 1 remains lower than a value $T_1$ (cf. FIG. 5), the resin impregnating the sample 11 maintains the viscosity which it presents at ambient temperature. Consequently, the transmission of the movement between the pair of jaws 5 and the pair of jaws 6 is simply effected with or without loss of amplitude. Consequently, as shown in FIG. 3 in its part 23, the pair of jaws 6 is animated by a reciprocating movement of constant amplitude B, less than the amplitude A of the reciprocating movement of the pair of jaws 5.

At temperature $T_1$ and time $t_1$, the resin impregnating the sample 11 begins to soften, thus reducing the rigidity of the sample. Consequently, the transmission of the reciprocating movement from the pair of jaws 5 to the pair of jaws 6 is damped and the amplitude B of the reciprocating movement of the pair of jaws 6 decreases. In FIG. 3, the corresponding zone is indicated by reference 24. The zone 24 ceases at time $t_2$ when the temperature $T_2$ corresponds to the beginning of polymerisation of the resin impregnating the sample 11. After time $t_2$, i.e. above temperature $T_2$, the resin therefore hardens and the transmission of the reciprocating movement from the pair of jaws 5 to pair of jaws 6 increases again. In FIG. 3, this zone corresponding to the polymerisation of the resin is represented by reference 25.

Figure 4:
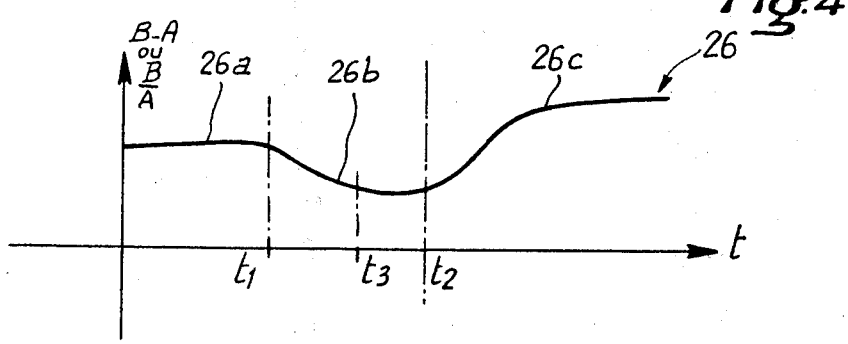
FIG. 4 is a comparison (difference or quotient) of the amplitude of movement transmitted through the sample and the constant amplitude applied thereto.

Thus, if, as in FIG. 4, the amplitudes A and B corresponding respectively to the reciprocating movement of the pair of jaws 5 and of the pair of jaws 6 are compared, for example by effecting the difference B-A or the ratio B/A, a curve 26 is obtained whose trend is characteristic of the different viscous states of the resin impregnating the sample 11. In its part 26a, the curve indicates that the resin presents a viscous state similar to the one which it has at ambient temperature; in its part 26b, it shows that the resin becomes liquid, whilst its part 26c indicates that the resin is polymerised and has become solid.

Figure 3:
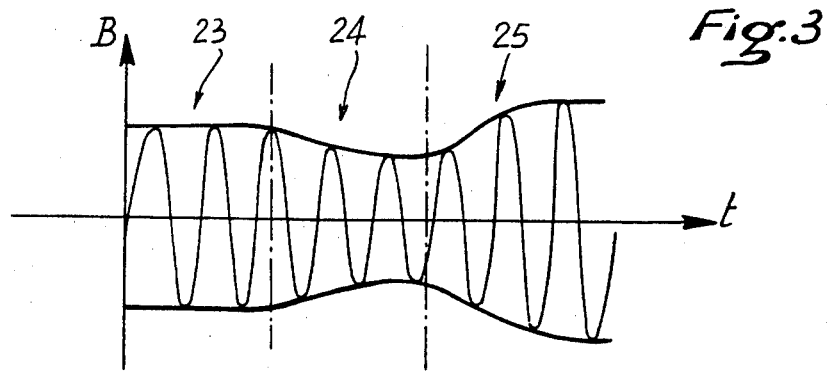
FIG. 3 is a graph of the amplitude of movement transmitted through the sample during the heating cycle.

Consequently, an examination of FIG. 3 (for example given directly by the recorder 19) or an examination of the curve 26 (for example given by the recorder 19 with which is associated a comparison device 27 receiving the information A via line 27a) will give the state of the resin as a function of temperature T.

Figure 5:
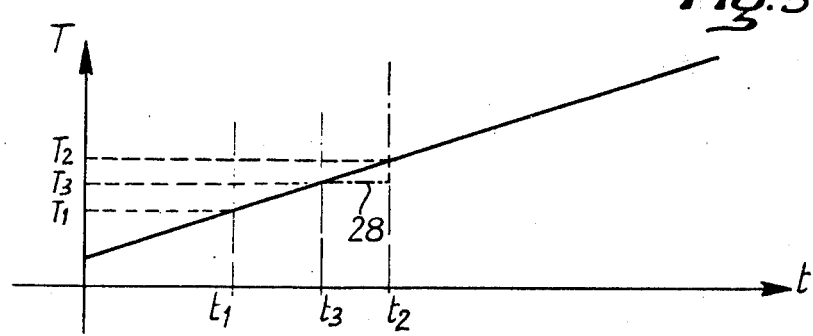
FIG. 5 is a graph showing the rising temperature existing during the heating cycle, correlated with the graphs of FIGS. 2, 3, and 4.

In the manufacture of articles by hot pressing resin-impregnated sheets, it is important to determine the range of temperatures over which the resin is soft or fluid. This temperature range is shown in FIG. 5 as that which exists between temperatures $T_1$ and $T_2$. Temperature $T_1$ corresponds to the beginning of softening of the resin impregnating the sample, shown in FIGS. 3 and 4 as the temperature at which a decrease in the amplitude of movement transmitted through the sample occurs. Temperature $T_2$ corresponds to the beginning of polymerization of the resin, indicated in FIGS. 3 and 4 as an increase in the amplitude of movement transmitted through the sample. Temperature $T_3$, corresponding to time $t_3$ in the heating cycle represents the optimum temperature at which hot pressing of superposed sheets of material should occur in order to produce the best properties in an article manufactured in this manner. At temperature $T_3$, which theoreticaly may occur at any value within the range between $T_1$ and $T_2$, the resin has its optimum viscosity for hot pressing. With any particular resin, the value of $T_3$ is determined by hot pressing a stack of two or more superposed sheets at each of several different temperatures within the range between $T_1$ and $T_2$ and determining by inspection of the finished article the optimum pressing temperature, corresponding to $T_3$.

When this temperature $T_3$ has been determined, it is possible to modify, at the moment of producing the shaped piece, the law of variation of the temperature as a function of time so as to maintain the temperature $T_3$ constant whilst the pressure is applied. FIG. 5 indicates this modification of the law of temperature by the broken line 28.

Due to the invention, it is thus possible accurately to determine the temperature $T_3$ at which the pressure must be applied on the stack of impregnated sheets with a view to obtaining the shaped piece.

Now, in order accurately to determine the value of the pressure to be applied, a plurality of presses 29 are used, which are disposed in the chamber 1. In FIG. 1, only one of these presses 29 has been shown. These presses comprise a frame 30 on which is mounted a hydraulic jack 31 supplied from the outside via pipes 32. The piston rod 33 of the jack 31 comprises at its end a pressure plate 34 adapted to press a sample 36 similar to sample 11 against a fixed support 35.

In this way, the samples 36 are subjected to the same law of temperature as the sample 11. At the moment when temperature $T_3$ corresponding to the optimum viscosity of the resin of samples 11 and 36 is attained, each of the samples 36 is subjected to a determined hydraulic pressure by means of the corresponding press 29.

At the end of the experiment, the different samples 36 are then examined, this enabling their state to be compared and making it possible to determine which is the optimum pressure to be applied on the stack of composite sheets intended to constitute the shaped piece.

The present invention therefore makes it possible to determine the optimum temperature and pressure to which a stack of sheets identical to samples 11 and 36 must be subjected with a view to obtaining a shaped piece.

What we claim is:

1. A method for measuring the effect of temperature on the viscoelasticity of a sheet material comprising a flexible reinforcement impregnated with a synthetic resin, which method comprises the steps of:

gripping a first sample of said sheet material between two spaced-apart zones in a plane and maintaining tension between said zones;

reciprocating one of said zones with a movement of constant amplitude in a direction coplanar with the plane of said sample and tranverse with respect to the tension therein;

subjecting said sample to a heating cycle including an increasing temperature;

and noting variations in amplitude of the reciprocating movement transmitted to the other of said zones as a measure of the viscoelasticity of said sample at different temperatures during said cycle.

2. A method in accordance with claim 1 for determining the range of temperatures in which the resin of said sheet material has an optimum viscosity for assembling by hot pressing, a plurality of superposed sheets of said sheet material, including the steps of:

subjecting a stack of two or more superposed samples of said sheet material to said heating cycle simultaneously with said first sample;

applying a controlled mechanical pressure to said stack at a selected temperature during said heating cycle;

cooling said stack after pressing and inspecting the properties thereof to determine the effect of variations in the magnitude of said pressure or the temperature at which said pressing occurs.

3. A method in accordance with claim 1, wherein said variations in amplitude of the reciprocating movement transmitted by said first sample to said other zone are observed directly.

4. A method in accordance with claim 1 wherein said variations in amplitude of the reciprocating movement transmitted by said first sample to said other zone are compared with said constant amplitude of reciprocation of said first zone and the results of the comparison are observed.

5. Apparatus for measuring the viscoelasticity of a sheet material comprising a flexible reinforcement impregnated with a synethetic resin, comprising:

means for subjecting a sample of said sheet material to a heating cycle including an increasing temperature;

a pair of gripping means for gripping said sample at spaced-apart zones and holding it under tension in a plane;

means for reciprocating one of said gripping means with a movement of constant amplitude in a direction coplanar with respect to the plane of said sample and transverse with respect to the tension therein; and means for detecting variations in amplitude of the reciprocating movement transmitted to the other of said gripping means through said sample during said heating cycle.

6. Apparatus in accordance with claim 5, wherein said means for subjecting said sample to a heating cycle includes a heating chamber;

said gripping means includes two spaced-apart coplanar pairs of jaws within said chamber, each of said pairs of jaws being adapted to be displaced parallel to the other in their common plane;

said means for reciprocating one of said gripping means includes a reciprocating movement generator mechanically connected to one of said pairs of jaws; and said means for detecting variations in amplitude of reciprocating movement includes a displacement pick-up mechanically connected to the other of said pairs of jaws.

7. Apparatus in accordance with claim 6 wherein said reciprocating movement generator comprises a motor and a crank-connecting rod system including a connecting rod disposed substantially in the common plane of said pairs of jaws and pivoted at one of its ends to one of said pairs of jaws;

said apparatus further including a displacement pick-up rod arranged parallel to said connecting rod and interconnecting said displacement pick-up and said other pair of jaws.

8. Apparatus in accordance with claim 7, wherein said reciprocating movement generator and said displacement pick-up are disposed outside said heating chamber and said connecting rod and said displacement pick-up rod pass through a wall of said chamber.

9. Apparatus in accordance with claim 6, wherein each of said pairs of jaws is connected to one end of at least one substantially planar spring leaf, the other end of which is operatively rigidly attached to said chamber, the plane of said spring leaf being at right angles to the plane of displacement of said jaws.

10. An apparatus in accordance with claim 6, including at least one press disposed within said chamber and adapted to apply pressure to a second sample of said sheet.

* * * * *